US00PP37418P2

(12) United States Plant Patent
Clarkson

(10) Patent No.: US PP37,418 P2
(45) Date of Patent: May 12, 2026

(54) ***FRAGARIA* PLANT NAMED 'CH67'**

(50) Latin Name: ***Fragaria* X *ananassa***
Varietal Denomination: CH67

(71) Applicant: Edward Vinson Ltd., Faversham (GB)

(72) Inventor: Graham Clarkson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 19/313,987

(22) Filed: Aug. 29, 2025

(30) Foreign Application Priority Data

Dec. 6, 2024 (QZ) ..... 2024/3044

(51) Int. Cl.
*A01H 5/08* (2018.01)

(52) U.S. Cl.
USPC ..... Plt./209

(58) Field of Classification Search
USPC ..... Plt./209
CPC ..... A01H 6/7409; A01H 5/08
See application file for complete search history.

*Primary Examiner* — Keith O. Robinson
(74) *Attorney, Agent, or Firm* — Penny J. Aguirre

(57) ABSTRACT

A new cultivar of *Fragaria* plant named 'CH67' that is characterized by its high marketable yields of fruit that is conical-shaped and very sweet in flavor, its very firm fruit with very good post-harvest shelf life, its plants that have strong vigor, a dense canopy and a semi-upright plant habit, its fruit that is orange red in color with a highly glossy surface, its leaves that are concave in the cross section, and its medium amount of blistering on the foliage.

3 Drawing Sheets

Botanical classification: *Fragaria* x *ananassa*.
Cultivar designation: 'CH67'.

CROSS-REFERENCE TO RELATED APPLICATIONS

This application claims priority to European Community Plant Variety Office (CPVO) Plant Breeder's Rights Application No. 2024/3044 filed on Dec. 6, 2024, under 35 U.S.C. 119(f), the entire contents of both applications which are incorporated by reference herein. This application is also related to Canadian Plant Breeder's Rights Application No. 25-11907 filed on Jan. 17, 2025. The information for the plant breeders' rights applications was received directly from the Inventor.

BACKGROUND OF THE INVENTION

The present invention relates to a new and distinct cultivar of *Fragaria*, botanically known as *Fragaria* x *ananassa*, and will be referred to hereafter by its cultivar name 'CH67'. 'CH67' is an everbearing variety which is primarily adapted to the climate and growing conditions of the United Kingdom and other regions of similar climate.

The new cultivar was derived from an ongoing breeding program conducted by the Inventor at a farm in Faversham, Kent, United Kingdom. 'CH67' arose from a controlled cross made by the Inventor in 2015 between an unpatented selection from the Inventor's breeding program, designated as accession number 'FL94', as the female parent and an unpatented selection from the Inventor's breeding program, designated as accession number 'EQ221', as the male parent. 'CH67' was selected in Faversham, Kent, United Kingdom as a single unique plant in the summer of 2016 from amongst the seedlings that resulted from the above cross.

Initial selection criteria included fruit number, uniformity of shape and color, fruit size, skin firmness and overall flavor.

Asexual propagation of the new cultivar was first accomplished the Inventor by rooting of stolons in Faversham, Kent, United Kingdom in spring of 2021. Asexual propagation of the new cultivar by rooting stolons and tissue culture using meristematic tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'CH67' as a new and unique cultivar of *Fragaria*.

1. 'CH67' exhibits high marketable yields of fruit that are conical-shaped and very sweet in flavor.
2. 'CH67' exhibits very firm fruit with very good post-harvest shelf life.
3. 'CH67' exhibits plants that have strong vigor, a dense canopy and a semi-upright plant habit.
4. 'CH67' exhibits fruit that is orange red in color with a highly glossy surface.
5. 'CH67' exhibits leaves that are concave in the cross section.
6. 'CH67' exhibits a medium amount of blistering on the foliage.

The female parent plant, 'FL94', differs from 'CH67' in fruit that have a smaller size, softer skin firmness, and a much more floral flavor. The male parent plant, 'EQ221', differs from 'CH67' in having leaves that are more convex in the cross section, fruit that is less even in appearance with raised achenes. 'CH67' can be most closely compared to the *Fragaria* x *ananassa* cultivar 'Eves Joy' (U.S. Plant Pat. No. 35,911) and 'Eves Delight 2' (U.S. Pat. No. 32,418). 'Eves Joy' is similar to 'CH67' in having early fruit production, fruit that is predominantly conical in shape with a fruit surface that is even and highly glossy, highly sweet flavor with a slight aroma, and achenes that are mostly below the surface with no band, in having leaves that are round in shape with serrate to crenate margins, a low number of stolons with sparse pubescence, a similar number of flowers per truss, and pollen produced in moderate quantity. 'Eves Joy' differs from 'CH67' in having a higher fruit yield, higher average fruit weight per plant, fruit that bruises more easily, a shorter shelf life, skin and flesh that are less firm, juicer fruit, less achenes, calyxes that are mostly level with the fruit, a less dense foliage canopy that is overall smaller in size, leaves that are larger in size, glossier surfaces, more interveinal blistering, margins that are more serrated, stolons with stronger anthocyanin coloration, longer and more narrow petioles and petiolules, flowers that are beneath the leaf canopy, and more flowers produced. 'Eves Delight 2' is similar to 'CH67' in having fruit with a highly sweet flavor, moderately juicy, a slight aroma, and a very good post-harvest shelf life. 'Eves Delight 2' differs from 'CH67' in having fruit that is smaller in size with a less glossy surface, a smaller plant size, a less dense foliage canopy, and typically larger leaves.

BRIEF DESCRIPTION OF THE DRAWINGS

The accompanying color photographs illustrate the overall appearance and distinct characteristics of the new *Fragaria*. The photographs were taken of plants 3 months in age (from a rooted module) as grown in coir bags and grown on tabletops under polyethylene covers in Faversham, Kent, United Kingdom.

The photograph in FIG. 1 provides a view of plant of 'CH67' in fruit.

Figure 1:
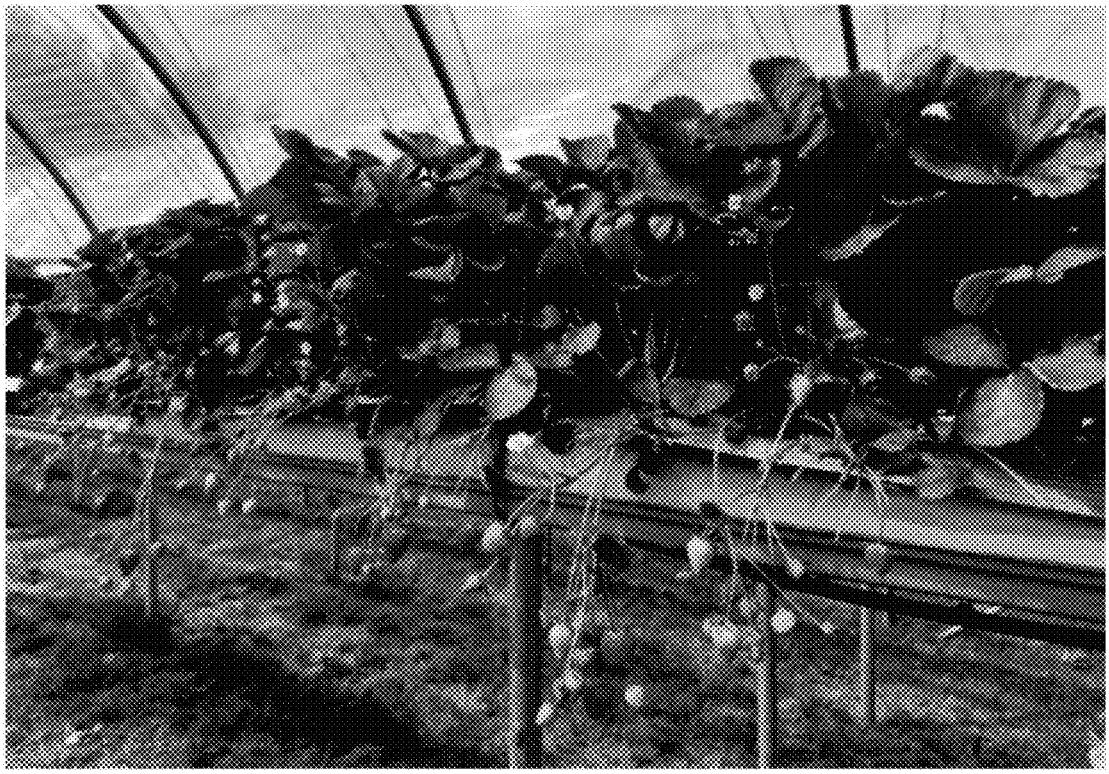
Figure 2:
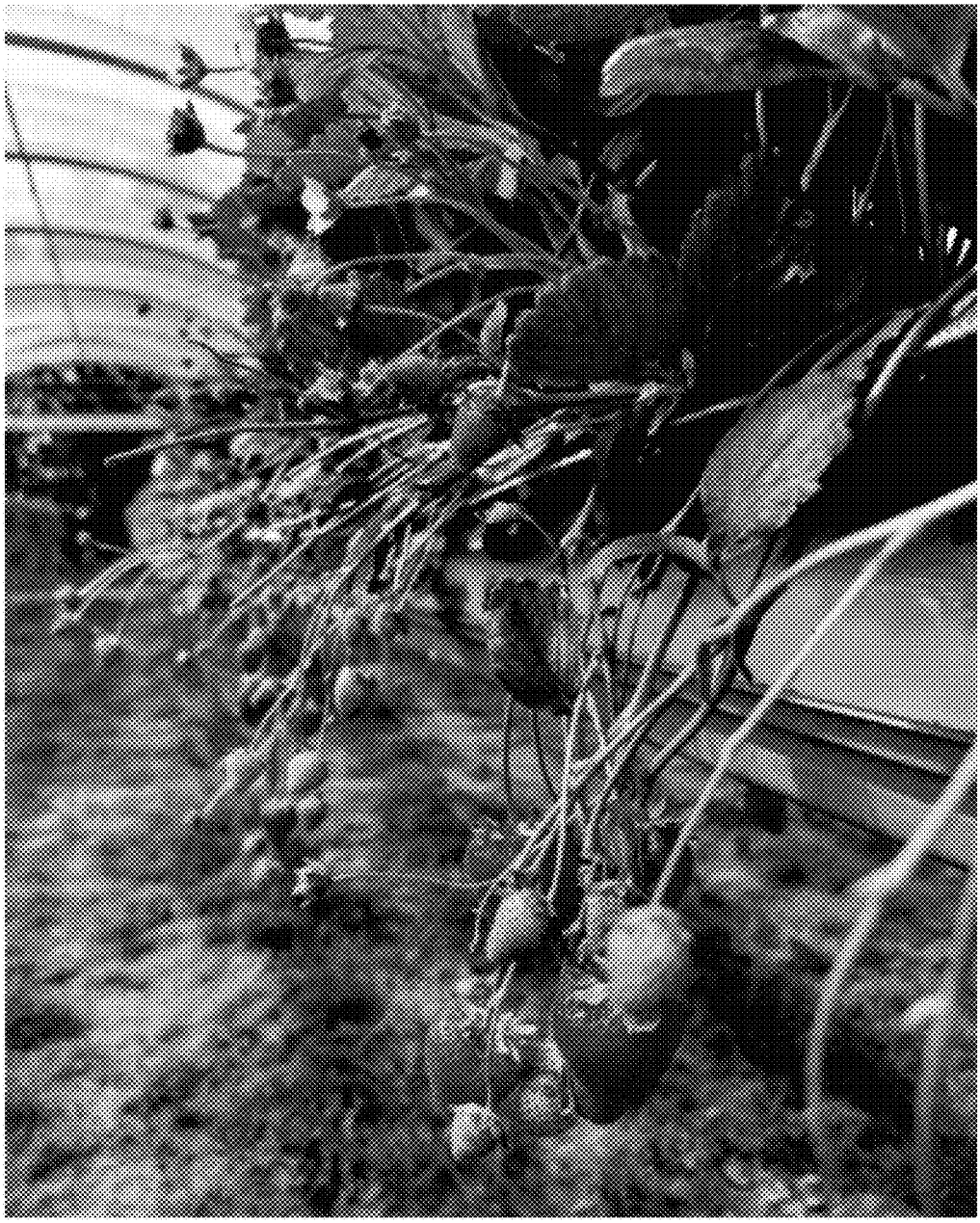

The photograph in FIG. 2 provides a view of the fruiting canes of 'CH67'.

Figure 3:
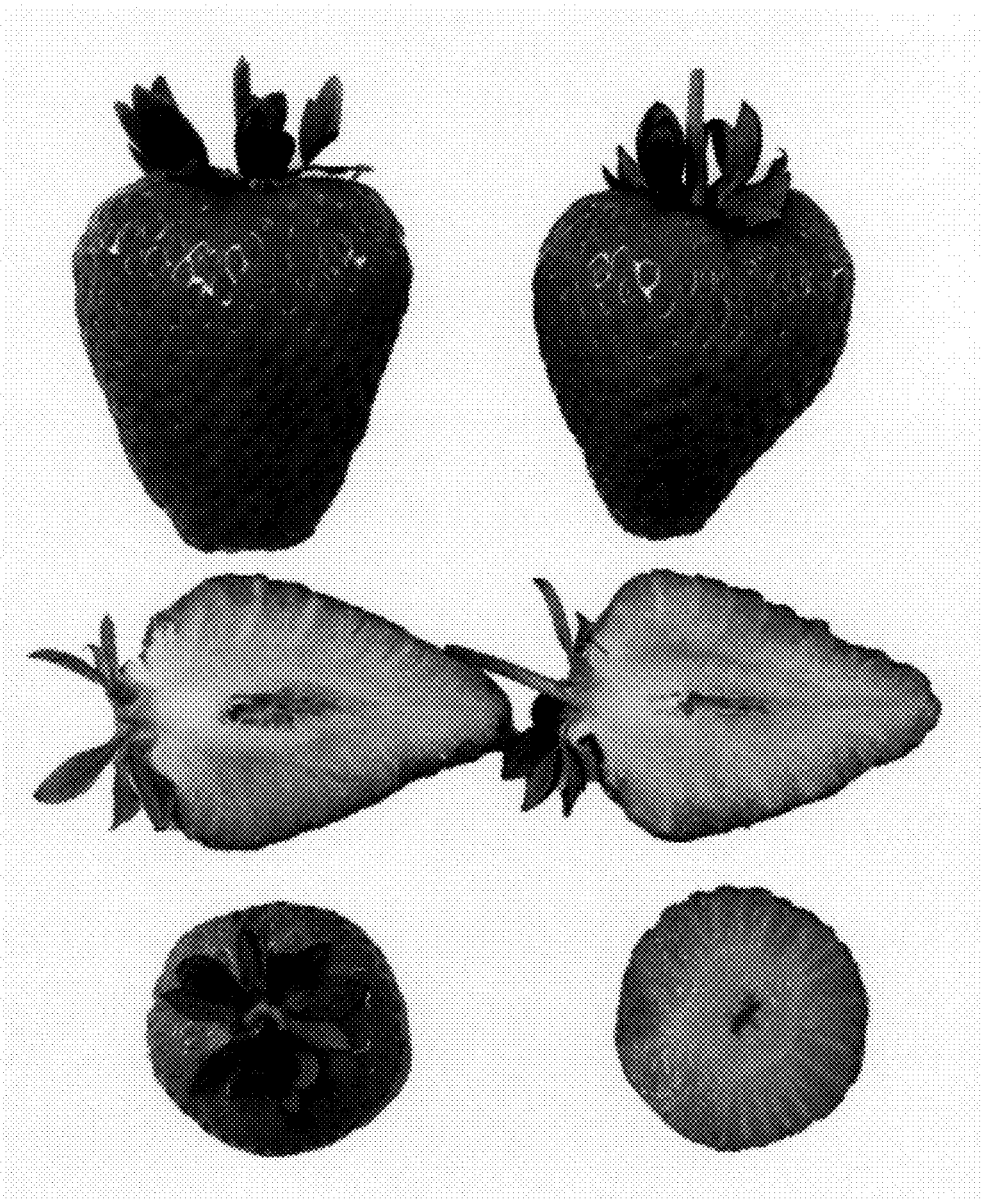

The photograph in FIG. 3 provides a close-up view of the fruit of 'CH67'; side view of whole fruit (top). longitudinally cut fruit (middle), horizontally cut fruit (bottom).

The colors in the photographs are as close as possible with the photographic and printing technology utilized and the colors may differ slightly from the color values cited in the detailed botanical description, which accurately describe the colors of the new *Fragaria*.

DETAILED BOTANICAL DESCRIPTION OF THE PLANT

The following is a detailed description of plants 3 months in age (from a rooted module) as grown on tabletops, in coir bags under tunnels with polyethylene covers in Faversham, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England (6th Edition), except where general color terms of ordinary dictionary significance are used.

General description:

*Blooming period*.—Starting in April and produced throughout the summer in Faversham, Kent, United Kingdom.

*Plant type*.—Herbaceous fruit-producing perennial.

*Plant habit and shape*.—Semi-upright with a dense canopy and strong vigor.

*Height and spread*.—Reaches an average of 43.1 cm in height and 9.36 cm in width, with an average height to width ratio of roughly 4.6:1.

*Hardiness*.—At least in U.S.D.A Zones 8 to 10 (not tested in areas with temps below 32° F. occur.

*Diseases and pests*.—Tolerance to *Botryotinia cinerea* and slight susceptibility to *Podosphaera leucotricha* (powdery mildew), as observed under conditions in Faversham, Kent, United Kingdom, no susceptibility or resistance to pests has been observed.

*Root description*.—Fibrous and vigorous, N155C in color.

*Propagation*.—Rooting of stolons and tissue culture.

*Root development*.—An average of 2 weeks to initiate roots and 5 weeks to produce a young, rooted plant from a rooted cutting.

*Growth rate*.—Vigorous.

*Stolons*.—An average of 9 per plant, 4 nodes per stolon, ranging between 17.45 cm to 3.49 cm between nodes, sparsely pubescent surface, 144A in color.

*Stem description*.—Acaulescent.

Foliage description:

*Leaf division*.—Compound, with three leaflets.

*Leaf shape*.—Trifoliate.

*Leaf arrangement*.—Basal.

*Leaf attachment*.—Petiolate.

*Leaf size*.—Average of 13.27 cm in length, 21.23 cm in width.

*Leaflet size*.—Terminal leaflet; average of 9.37 cm in length, 8.57 cm in width, lateral leaflet; average of 8.76 cm in length, 8.48 cm in width.

*Leaflet shape*.—Rounded.

*Leaflet margins*.—Serrate to crenate with an average of 19.8 serrations per leaf.

*Leaflet base*.—Acute.

*Leaflet apex*.—Round.

*Leaflet aspect*.—Concave.

*Leaflet interveinal blistering*.—Medium.

*Leaflet venation*.—Pinnate, both surfaces match leaf color.

*Leaflet surface*.—Both surfaces slightly glossy, upper surface glabrous, lower surface slightly pubescent, main vein moderately pubescent.

*Leaflet rugosity*.—Weak.

*Leaflet color*.—Upper surface; 137A, lower surface; 138B.

*Petiole*.—Round in shape, N144D in color, average of 20.22 cm in length, 5.3 mm in width, surface weak to moderately covered with soft pubescence with hairs adpressed to upright.

*Petiolules*.—Round in shape, N144D in color, average of 2.12 cm in length and 8.3 mm in width, surface weak to moderately covered with soft pubescence.

*Stipule*.—Average of 1.38 cm in length and 8 mm in width, 37B in color.

*Variegation*.—None.

Flower description:

*Inflorescence*.—Truss, 18.97 cm in length, 30.53 cm in width, including peduncle and pedicel.

*Pedicel*.—Moderately strong, average of 8.21 cm in length, 2.1 mm in width, 150C in color, surface moderately covered with soft pubescence.

*Peduncle*.—Strong, an average of 6.76 cm in length, 4.2 mm in width, 150C in color, surface moderately covered with soft pubescence.

*Flower initiation and expression conditions*.—Temperature dependent.

*Time of flowering* (50% *of plants at first flower*).—Early season.

*Flower position relative to foliage*.—Same level as the leaf canopy.

*Flower size*.—Average of 2.07 cm in diameter and 1.2 cm in depth.

*Flower number per truss*.—6.

*Flower fragrance*.—Weak, sweet and fruity (strawberry-like).

*Calyx*.—Average of 2.69 cm in diameter, larger in relation to the corolla on primary and secondary flowers and smaller on the tertiary flowers.

*Sepals*.—Average of 11 per flower, average of 8.8 mm in length and 4.9 mm in width, obtuse base, acute apex, color; upper surface 137A, margins 154C, center 138B, lower surface 138A.

*Sepal position*.—Mixed arrangement relative to fruit, most re-curving and some horizontal with fruit shoulder.

*Petals*.—5, average of 1.14 cm in length and 1.29 cm in width, obtuse base, acute apex, overlapping in arrangement, entire margins, glabrous upper and lower surfaces, 155B in color.

*Bracts*.—Observed on majority of the flowering trusses at point of branching from early developmental stage, which progresses into a small single leaflet as the truss matures and fruit develops, average of 2.65 cm in length and 1.94 cm in width, both surfaces 137A in color.

Reproductive organs:

*Gynoecium*.—Average of 5 mm in height and 5.9 mm in width, dome-shaped, apocarpous with multiple simple carpels present with capitate shaped stigma.

*Androecium*.—Stamens; average of 21.8 per flower, anthers average of 3.3 mm in length, 12A in color, pollen; moderate in quantity.

Fruit description

*Shape*.—Mostly conical and similar for primary, secondary and tertiary fruit, apex of the fruit is mostly acute, with some obtuse, calyx of the fruit is mostly rounded when excluding the neck.

*Season of harvest*.—May through to End September in Faversham, Kent.

*Time of ripening* (50% *of plants with first ripe fruit*).—Early.

*Type of bearing*.—Everbearing.

*Size*.—Large, average of 4.71 cm in length and 3.92 cm in width.

*Surface*.—Smooth with strong glossiness.

*Calyx position*.—Mixed, primary fruit mostly inserted, secondary and tertiary fruit level or raised.

*Attitude of calyx segments*.—Mostly upwards.

*Diameter of calyx relative to fruit diameter*.—Mixed.

*Glossiness*.—Even and strong gloss.

*External color* (*skin*).—34A, color is retained throughout the cropping season.

*Internal color* (*flesh*).—Near skin; 30A, near core; 29C.

*Evenness of color of skin*.—Very even.

*Evenness of color of flesh*.—Paler near center, 29C in color.

*Acidity*.—0.495% TTA.

*Sweetness*.—High.

*Soluble solids*.—Average of 9° over three seasons in trials.

*Firmness*.—Skin is very firm (resistant to bruising), flesh is very firm.

*Juiciness*.—Moderate.

*Aroma*.—Slight.

*Weight*.—Average of 18.2 g per berry and 1195 g per plant from late May to end of September over three seasons in trials.

*Number of fruits per plant*.—Average of 65.7 fruits per plant from late May to end of September over three seasons in trials.

*Hollow center*.—Slight on primary, secondary and tertiary fruit, more prominent on primary fruit.

*Shelf life*.—Very good, at least 7 days in cold storage.

*Achene color*.—Ranges from 42A to 1B.

*Achene position*.—Majority below the surface.

*Achene number*.—An average of 314.8 per berry.

*Band without achenes*.—Absent.

*Market use*.—High shipping quality fruit for fresh consumption.

It is claimed:

1. A new and distinct cultivar of *Fragaria* plant named 'CH67' as herein illustrated and described.

* * * * *